(12) United States Patent
Hirokawa et al.

(10) Patent No.: US 8,270,560 B2
(45) Date of Patent: Sep. 18, 2012

(54) X-RAY CT SCAN SIMULATOR AND X-RAY CT APPARATUS

(75) Inventors: Koichi Hirokawa, Tokyo (JP); Taiga Goto, Tokyo (JP); Yoshiaki Sugaya, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 12/866,484

(22) PCT Filed: Feb. 25, 2009

(86) PCT No.: PCT/JP2009/053407
§ 371 (c)(1),
(2), (4) Date: Aug. 6, 2010

(87) PCT Pub. No.: WO2009/107658
PCT Pub. Date: Sep. 3, 2009

(65) Prior Publication Data
US 2010/0322375 A1    Dec. 23, 2010

(30) Foreign Application Priority Data
Feb. 25, 2008  (JP) .................................. 2008-042308

(51) Int. Cl.
*A61B 6/00* (2006.01)
*G06K 9/00* (2006.01)
(52) U.S. Cl. ................................ 378/4; 378/19; 382/131
(58) Field of Classification Search ................... 378/4, 19
See application file for complete search history.

(56) References Cited

U.S. PATENT DOCUMENTS

| 5,864,597 | A  | * | 1/1999  | Kobayashi ........................ 378/4 |
| 6,904,162 | B2 | * | 6/2005  | Robar et al. .................. 382/128 |
| 2004/0017880 | A1 | * | 1/2004  | Toth et al. ......................... 378/4 |
| 2005/0008115 | A1 | * | 1/2005  | Tsukagoshi ....................... 378/4 |
| 2007/0071160 | A1 | * | 3/2007  | Nishide et al. .................... 378/4 |
| 2009/0245459 | A1 | * | 10/2009 | Goto et al. ...................... 378/16 |

FOREIGN PATENT DOCUMENTS

| JP | 2008-48880 | 3/2008 |
| WO | WO2007/074772 | 7/2007 |
| WO | WO2007/114470 | 10/2007 |

OTHER PUBLICATIONS

Junko et al., English Translation of JP2008048880, 2008, pp. 1-8.*

\* cited by examiner

*Primary Examiner* — Alexander H Taningco
(74) *Attorney, Agent, or Firm* — Cooper & Dunham LLP

(57) ABSTRACT

There are provided an X-ray CT scan simulator and an X-ray CT apparatus in which a lesion postulated by an operator can be displayed on a simulation image and a high-precision simulation containing a postulation of occurrence of a new lesion can be performed. They comprise an image storing device for storing a reference image, a target noise value setting device for setting a target noise value of a desired image, a simulated lesion setting device for setting a condition for a simulated lesion postulated by the operator, a simulation image generating device for generating a simulation image containing a simulated lesion by using the reference image on the basis of the set target noise value and the condition for the simulated lesion, and an image display device for displaying the simulation image containing the simulated lesion.

7 Claims, 7 Drawing Sheets

X-RAY CT SCAN SIMULATOR AND X-RAY CT APPARATUS

TECHNICAL FIELD

The present invention relates to an X-ray computer tomography device (CT), and particularly to a technique of obtaining an image corresponding to an imaging condition by simulation.

BACKGROUND ART

Recently, X-ray CT apparatus have been able to collect data in a broad range in a short time because of a multi-row structure of X-ray detectors and increase of scanner rotational speed. On the other hand, the exposed dose per examination has increased and thus importance has been put to reduction of X-ray exposure due to a dose-reduced imaging operation. However, simple low-dose imaging causes increase of image noise and thus an image suitable for diagnosis cannot be obtained in some cases.

Therefore, there has been proposed a technique that an image to be obtained under any imaging condition specified by an operator is simulated before the image is picked up as disclosed in Patent Document 1. According to this technique, an image to be obtained under the specified imaging condition can be presented to the operator before the image is picked up, and thus the operator can determine whether an image suitable for diagnosis can be obtained under the specified imaging condition.

Patent Document 1: JP-A-2004-057831
Patent Document 2: JP-A-2006-116137

However, the technique disclosed in Patent Document 1 gives no consideration to what a lesion assumed by an operator looks like on a simulation image, that is, execution of a simulation based on the assumption of occurrence, metastasis or the like of tumor.

BRIEF SUMMARY

In an aspect of this disclosure, there is provided an X-ray CT scan simulator and an X-ray CT apparatus that can display a lesion postulated by an operator on simulation images and can perform high-precision simulations containing postulations of occurrence of new lesions.

In another aspect, an X-ray CT scan simulator includes: an image storing device for storing a reference image; a target noise value setting device for setting a target noise value of a desired image; a simulated lesion setting device for setting a condition for a simulated lesion postulated by the operator; a simulation image generating device for generating a simulation image containing a simulated lesion by using the reference image on the basis of the set target noise value and the condition for the simulated lesion; and an image display device for displaying the simulation image containing the simulated lesion.

In another aspect, an X-ray CT apparatus comprises: an X-ray source for irradiating an object to be examined with X-ray; an X-ray detector that is disposed so as to face the X-ray source and detects X-ray transmitted through the object; a rotating device that rotates around the object and in which the X-ray source and the X-ray detector are mounted; an image re-constructing device for re-constructing a tomogram of the object on the basis of transmitted X-ray doses in plural directions that are detected by the X-ray detector; an imaging condition input device for inputting an irradiation condition of the X-ray and a condition for image reconstruction; and an image display device for displaying the tomogram, and is characterized by further comprising: an image storing device for storing a reference image; a target noise value setting device for setting a target noise value of a desired image; a simulated lesion setting device for setting a condition for a simulated lesion postulated by the operator; and a simulation image generating device for generating a simulation image containing a simulated lesion by using the reference image on the basis of the set target noise value and the condition for the simulated lesion, wherein the image display device displays the simulation image containing the simulated lesion.

Thus, a lesion postulated by an operator can be displayed on a simulation image, and high-precision simulation containing the postulation of occurrence of a new lesion can be performed.

DESCRIPTION OF REFERENCE NUMERALS

1 X-ray CT apparatus, 100 scan gantry portion, 101 X-ray tube, 102 rotational disc, 103 collimator, 104 opening portion, 105 bed, 106 X-ray detector, 107 data collecting device, 108 gantry control device, 109 bed control device, 110 X-ray control device, 120 operating table, 121 input device, 122 image calculating device, 123 storage device, 124 system control device, 125 display device, 2 X-ray CT scan simulator, 200 simulation image generating device, 201 object model calculating means, 202 image noise calculating means, 203 added noise amount calculating means, 204 reference projection data creating means, 205 noise projection data creating means, 206 simulated lesion projection data creating means, 207 projection data adding means, 208 image reconstructing means, 209 simulation image creating means, 210 image storing device, 220 condition setting device, 230 simulation image display device, 400 condition setting screen for simulated lesion, 410 reference image display area, 411 reference image, 412 simulated lesion coordinate setting cursor, 420 simulated lesion condition setting area, 421 x coordinate setting box, 422 y coordinate setting box, 423 size setting box, 424 CT value difference setting box, 425 shape setting box

MODES FOR CARRYING OUT THE INVENTION

Preferred embodiments according to the present invention will be described with reference to the accompanying drawings.

<<Hardware Construction>>

Figure 1:
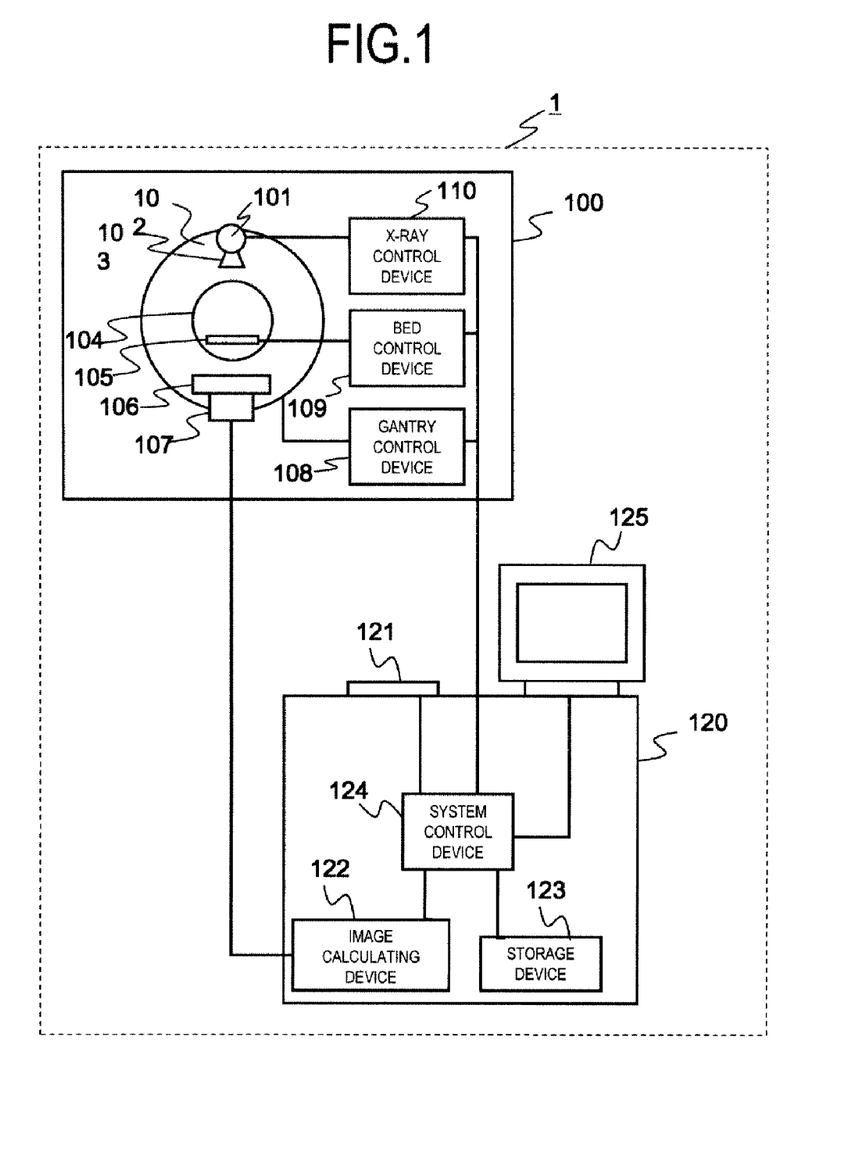
FIG. 1 is a diagram showing the construction of an X-ray CT apparatus according to the present invention.

FIG. 1 is a diagram showing the overall construction of an X-ray CT apparatus 1 to which the present invention is applied. The X-ray CT apparatus 1 has a scan gantry portion 100 and an operating table 120.

The scan gantry portion 100 has an X-ray tube 101, a rotational disc 102, a collimator 103, an X-ray detector 106, a data collecting device 107, a bed 105, a gantry control device 108, a bed control device 109 and an X-ray control device 110. The X-ray tube 101 is a device for irradiating an object laid on the bed 105 with X-ray. The collimator 103 is a device for controlling the irradiation direction of X-ray emitted from the X-ray tube 101. The X-ray detector 106 is a device for detecting X-ray transmitted through the object which is disposed so as to face the X-ray tube 101, and generates an electrical signal corresponding to the dose of transmitted X-ray. The rotational disc 102 has an opening portion 104 which the object laid on the bed 105 enters, and rotates around the object while the X-ray tube 101 and the X-ray detector 106 are mounted on the rotational disc. The data collecting device 107 is a device for converting X-ray detected by the X-ray detector 106 to a predetermined signal. The gantry control device 108 is a device for controlling the rotation of the rotational disc 102. The bed control device 109 is a device for controlling the motions in the up-and-down direction and the front-and-rear direction of the bed 105. The X-ray control device 110 is a device for controlling the output to the X-ray tube 101.

The operating table 120 has an input device 121, an image calculating device 122, a display device 125, a storage device 123 and a system control device 124. The input device 121 is a device for inputting the name of the object, the date and hour of examination, an imaging condition, a condition for a simulated lesion, etc., and specifically, it is a keyboard, a pointing device or the like. The image calculating device 122 is a device for processing measurement data transmitted from the data collecting device 107 to reconstruct a CT image. The display device 125 is a device for displaying a CT image created by the image calculating device 122. The storage device 123 is a device for storing data collected by the data collecting device 107 and image data of the CT image created by the image calculating device 122. The system control device 124 is a device for controlling these devices, the gantry control device 108, the bed control device 109 and the X-ray control device 110.

The X-ray tube 101 is controlled by the X-ray control device 110 so as to emit X-ray which is based on the imaging condition (an X-ray tube voltage, X-ray tube current, etc.) input from the input device 121. The X-ray detector 106 has many (for example, 1000) X-ray detecting elements which are arranged in the peripheral direction of the rotational disc 102 or two-dimensionally arranged in the peripheral direction of the rotational disc 102 and in the rotational axis direction of the rotational disc 102, and detects through the respective detection elements X-ray which is emitted from the X-ray tube 101 and transmitted through the object. The rotational disc 102 is controlled by the gantry control device 108, and rotated on the basis of an imaging condition (scan speed, etc.) input from the input device 121. The bed 105 is controlled by the bed control device 109, and operated on the basis of an imaging condition (spiral pitch, etc.) input from the input device 121.

The emission and detection of the X-ray are performed while the rotational disc 102 is rotated around the object, whereby X-ray projection data from various directions (for example, the direction of 1000) are collected by the data collecting device 107. The X-ray projection data collected by the data collecting device 107 are transmitted to the image calculating device 122. The image calculating device 122 subjects the X-ray projection data to reconstructing calculation to obtain a CT image. The reconstructed CT image is displayed on the display device 125, and stored as image data in the storage device 123 together with the imaging condition.

<<Construction of X-Ray CT Scan Simulator>>

Figure 2:
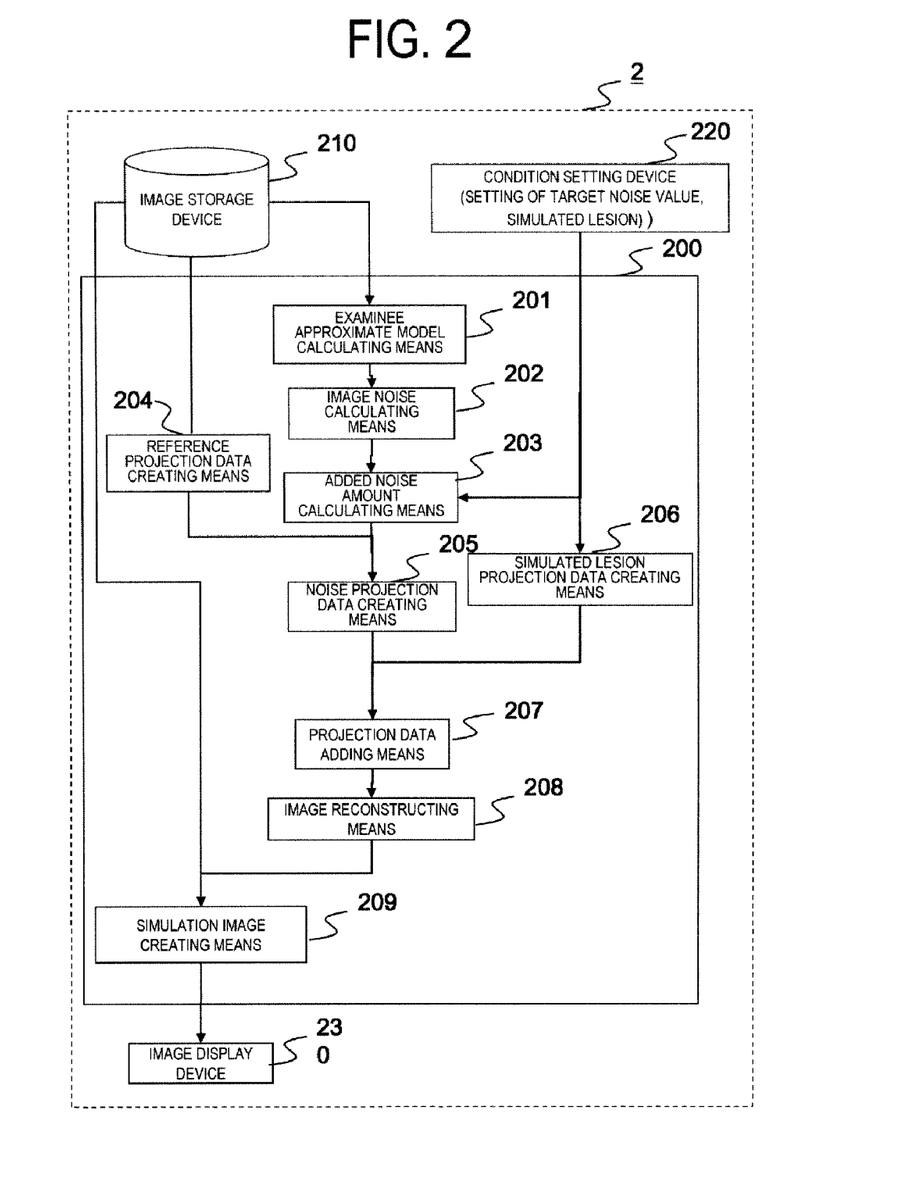
FIG. 2 is a diagram showing the construction of an X-ray CT scan simulator according to the present invention.

FIG. 2 is a diagram showing the construction of an X-ray CT scan simulator 2 for simulating an image which is obtained through an image pickup operation before the image pickup operation using the X-ray CT apparatus 1 is executed. The X-ray CT scan simulator 2 has an image storage device 210, a condition setting device 220, a simulation image generating device 200 and a simulation image display device 230.

The image storage device 210 is a device for storing a reference image as a reference of a simulation image created by the X-ray CT scan simulator 2, and specifically it is HD (Hard Disk) or the like. The reference image is a past image which was obtained by subjecting the object to CT imaging in the past or a human body phantom image obtained by beforehand performing CT imaging on a human phantom which faithfully reproduces an internal tissue of a human body. A sufficient X-ray dose is used to pick up the human body phantom image so that a clear image is obtained. A human phantom image obtained through the imaging based on representative FOV may be prepared every site. The storage device 123 may be used as the image storage device 210.

The condition setting device 220 is a device for setting a target noise value and a condition for a simulated lesion by an operator, and specifically it is a keyboard, a pointing device or the like. The target noise value may be an image SD (Standard Deviation) value input by the operator or an imaging condition (tube voltage, tube current, slice thickness, scan time, etc.) set in the X-ray CT apparatus by the operator and an image SD value calculated on the basis of an approximate model of the object described later. As the condition for the simulated lesion may be used the coordinate, shape and size of the simulated lesion, the difference in CT value of the simulated lesion from the surrounding tissue etc. The input device 121 may be used as the condition setting device 220.

The simulation image generating device 200 is a device for generating a simulation image on the basis of the reference image, the target noise value and the condition for the simulated lesion, and specifically it is CPU for executing calculation processing described later or a dedicated calculation circuit. The simulation image generating device 200 has object approximate model calculating means 201, image noise calculating means 202, added noise amount calculating means 203, reference projection data creating means 204, noise projection data creating means 205, simulated lesion projection data creating means 206, projection data adding means 207, image reconstructing means 208 and simulation image creating means 209. The simulation image generating device 200 may be mounted in the image calculating device 122 or the system control device 124 of the X-ray CT apparatus 1, or mounted on another device other than the X-ray CT apparatus 1 so as to communicate with the X-ray CT apparatus 1 through LAN (Local Area Network).

The object approximate model calculating means 201 determines an approximate transmission length of homogeneous medium (for example, water) of a cross-section of the object from the reference image to calculate an object approximate model having the determined approximate transmission length. The method of calculating the object approximate model will be described later.

The image noise calculating means 202 calculates an image noise value owned by the reference image. The method of calculating the image noise will be described later.

The added noise amount calculating means 203 calculates a noise amount to be added to the reference image to create an image which implements a desired image noise value. The method of calculating the noise amount to be added will be described later.

The reference projection data creating means 204 creates reference projection data on the basis of the reference image. The method of calculating the reference projection data will be described later.

The noise projection data creating means 205 creates noise projection data for a noise image to be added to the reference image while considering the value of the reference projection data. The method of calculating the noise projection data will be described later.

The simulated lesion projection data creating means 206 creates projection data for a simulated lesion on the basis of the condition for the simulated lesion (the coordinate, the shape, the size, the difference in CT value from the surrounding tissue, etc.) set through the condition setting device 220. The simulated lesion projection data are created as projection data containing no noise. The method of calculating the simulated lesion projection data will be described later.

The projection data adding means 207 adds the noise projection data with the simulated lesion projection data to create the added image projection data.

The image reconstructing means 208 applies the added image projection data to the reconstruction processing (for example, Filtered Back Projection method) to create addition image to be added to the reference image. The image calculating device 122 may be used as the image reconstructing means 208.

The simulation image creating means 209 adds the reference image with the addition image to create a simulation image. The created simulation image is an image satisfying the image noise value and the condition for the simulated lesion which are set through the condition setting device 220.

The simulation image display device 230 is a device for displaying a simulation image generated by the simulation image generating device 200, and specifically it is CRT (Cathode Ray Tube), a liquid crystal display or the like. The display device 125 may be used as the simulation image display device 230.

<<Flow of Processing>>

Figure 3:
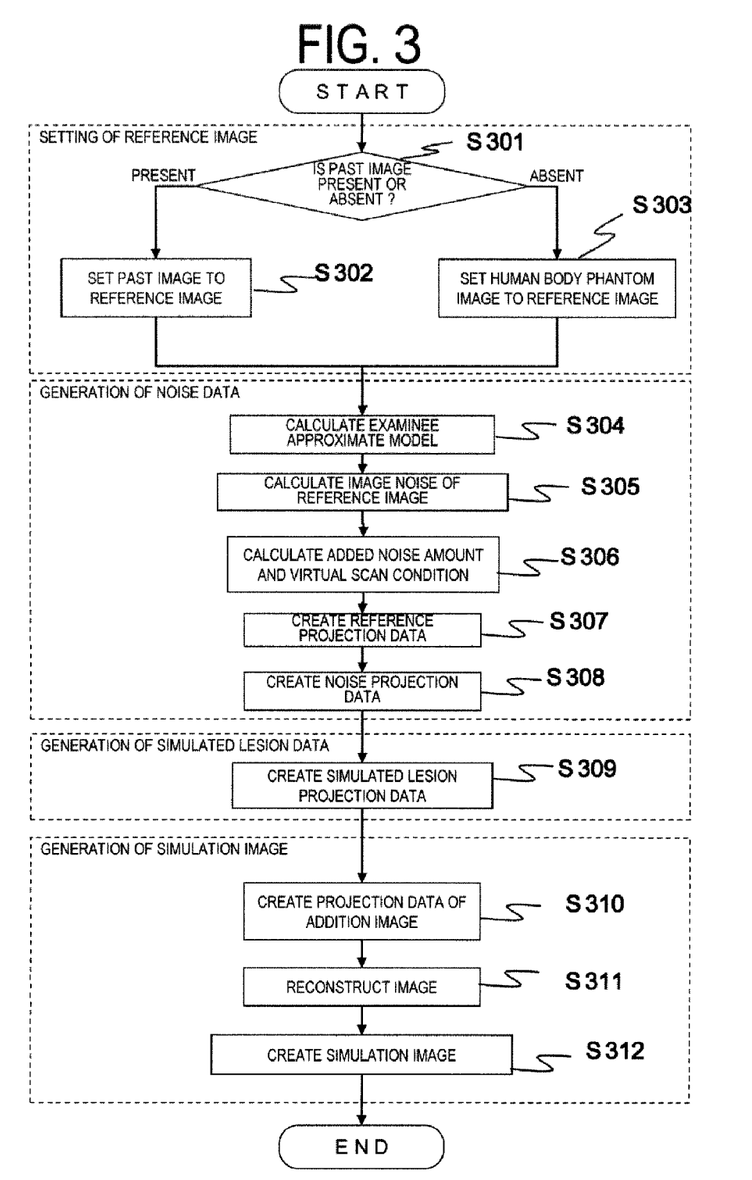
FIG. 3 is a diagram showing the processing flow showing a method of creating a simulation image.

FIG. 3 shows the flow of the processing until the simulation image is generated by this embodiment. A rough flow contains the setting of a reference image in steps S301 to S303, the generation of noise data in steps S304 to S308, the generation of simulated lesion data in step S309 and the generation of a simulation image in steps S310 to S312.

Figure 4:
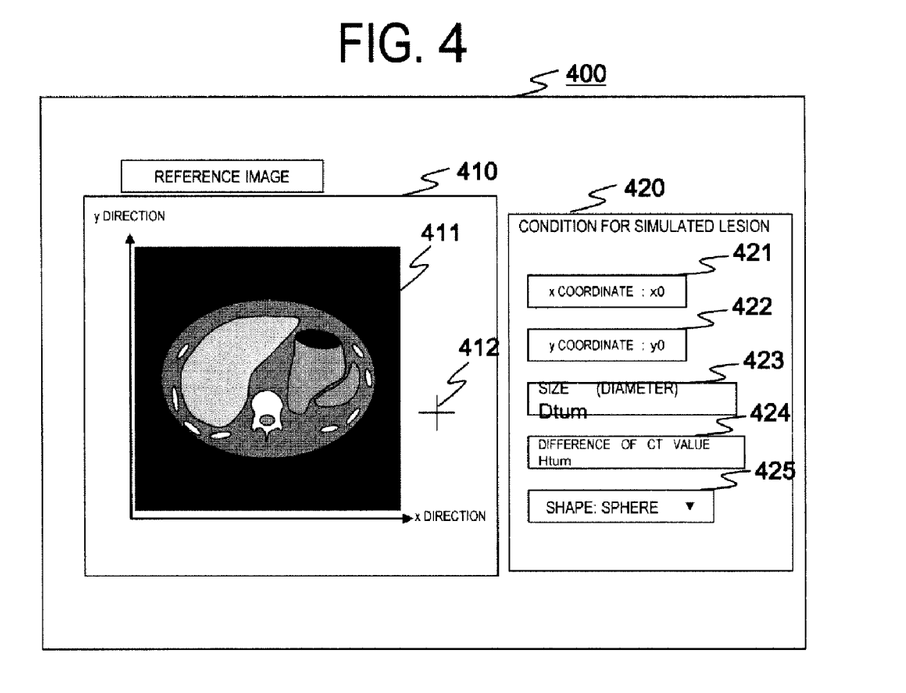
FIG. 4 is a diagram showing an example of a condition setting screen for a simulated lesion.

The target noise value and the condition for the simulated lesion (the coordinate, the size, the difference in CT value from the surrounding tissue) are assumed to be preset through the condition setting device 220. FIG. 4 shows an example of the condition setting screen for the simulated lesion. A condition setting screen 400 for the simulated lesion is constructed by a reference image display area 410 and a simulated lesion condition setting area 420, and displayed on the image display device 230. A selected reference image 411 is displayed in the reference image display area 410, and various kinds of boxes 421 to 425 used to set various kinds of conditions for the simulated lesion are displayed in the simulated lesion condition setting area 420. As the various kinds of boxes are displayed an x-coordinate setting box 421 and a y-coordinate setting box 422 for setting the coordinate of the simulated lesion, a box 423 for setting the size of the simulated lesion, a box 424 for setting the difference in CT value between the simulated lesion and the surrounding tissue, and a box 425 for setting the shape of the simulated lesion. The boxes 421 to 424 are boxes for editing numerical values. The box 425 is a box for selecting a menu. The operator can set a desired condition for a simulated lesion by operating these boxes. The coordinate of the simulated lesion may be set according to a method of clicking a desired position within the reference image 411 with a mouse to set a simulated lesion coordinate setting cursor 412, or the like.

Each step of FIG. 3 will be described hereunder.
(Step S301)
The X-ray CT scan simulator 2 searches past images of the object as a simulation target in the image storage device 210, and determines whether there is a past image pickup record for the same site. When some past image exists as a determination result, the processing goes to step S302, and when there is no past image, the processing goes to step S303.
(Step S302)
The X-ray CT scan simulator 2 sets the past image to the reference image.
(Step S303)
The X-ray CT scan simulator 2 sets the human body phantom image to the reference image.
(Step S304)
The object approximate model calculating means 201 calculates the object approximate model on the basis of the reference image set in S302 or S303 as follows.

Figure 5:
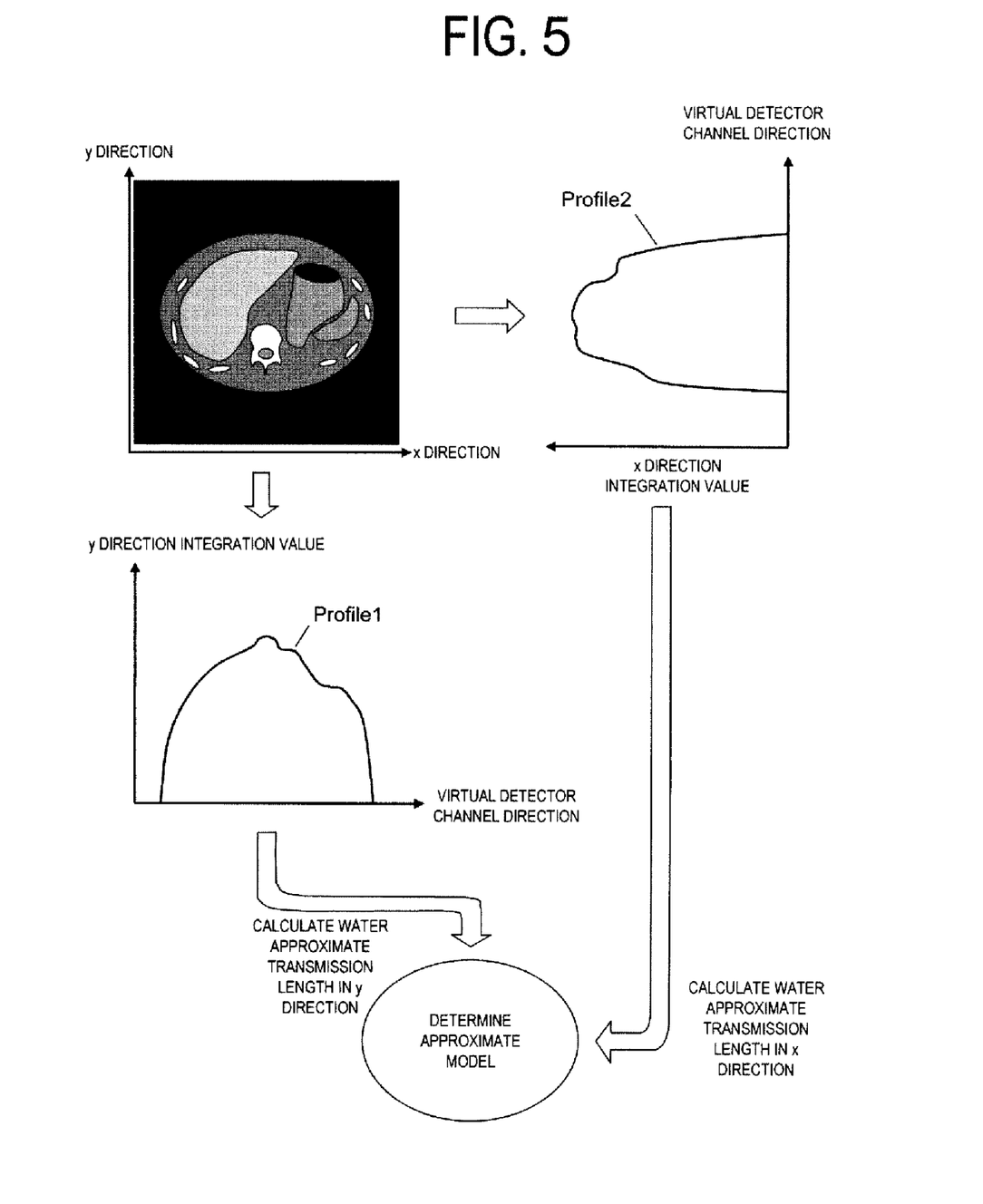
FIG. 5 is a diagram showing the summary of an approximate model calculating method.

FIG. 5 shows the outline of the approximate model calculating method. First, CT values of the reference image are integrated in the y direction to obtain profile1 according to the mathematical expression 1.

[Mathematical Expression 1]
$$profile1(vch) = ypt * \sum_{iy=0}^{YMTX-1} \left( \frac{\text{org\_img}(vch, iy)}{1000} + 1 \right)$$

Here,
vch: virtual detector channel number, vch=0, 1, . . . , XMTX−1
XMTX: the number of pixels in the x direction
ypt: the pixel pitch in the y direction
YMTX: the number of pixels in the y direction
org_img(vch,iy): CT value of reference image at x coordinate=vch, y coordinate=iy Next, the CT value of the reference image is integrated in the x direction according to the mathematical expression 2 to obtain profile2.

[Mathematical Expression 2]
$$profile2(vch) = xpt * \sum_{ix=0}^{XMTX-1} \left( \frac{\text{org\_img}(ix, vch)}{1000} + 1 \right)$$

Here, vch: virtual detector channel number, vch=0, 1, ..., YMTX-1

YMTX: the number of pixels in the y direction xpt: the pixel pitch in the x direction XMTX: the number of pixels in the x direction org_img(ix,vch): CT value of reference image at x coordinate=ix, y coordinate=vch Next, the transmission length ypd in the y direction and the transmission length xpd in the x direction are calculated according to the mathematical expression 3, and these values are set as diameters in the y direction and the x direction of an elliptical approximate model. In this embodiment, it is assumed that the approximate model is constructed by water, however, it is not limited to water.

$$ypd = n\text{maxave}(\text{profile1}, n)$$

$$xpd = n\text{maxave}(\text{profile2}, n) \quad \text{[Mathematical Expression 3]}$$

Here, nmaxave(prf,n): function of calculating simple addition average based on data of n in descending order of the value of data row prf.

(Step S305)

The image noise calculating means 202 calculates the image noise amount of the object approximate model calculated in S304 as follows. In order to calculate the noise amount to be added to the reference image to implement a target image SD, it is required to first calculate an image noise variance in the reference image, that is, a square value of the image SD in the reference image. Therefore, the image noise variance Vorg_img in the reference image is calculated on the basis of the above elliptical approximate model in consideration of the transmission length of each view used for image reconstruction, the X-ray tube voltage, the X-ray tube current, view weighting under reconstruction, etc. according to the method disclosed in Patent Document 2, for example.

(Step S306)

The added noise amount calculating means 203 calculates a noise amount to be added to the reference image on the basis of the image noise amount of the reference image calculated in S305 and a preset target noise value. Furthermore, it calculates a virtual scan condition for creating noise projection data corresponding to the noise amount to be added. The calculation method will be described below.

When a target image SD is set as SDtgt, the target image noise variance Vtgt is represented by the mathematical expression 4.

$$Vtgt = SDtgt^2 \quad \text{[Mathematical Expression 4]}$$

Accordingly, in order to implement the target image noise, a noise image having an image noise variance Vn_img represented by the mathematical expression 5 may be created.

$$Vn\_img = Vtgt - Vorg\_img \quad \text{[Mathematical Expression 5]}$$

When the product between the tube current and the time for the reference image is represented by xmAs0, the product xmAs_ni between the tube current and the time for the noise image to be added to the reference image is represented by the mathematical expression 6.

$$xmAs\_ni = xmAs0 * Vorg\_img / Vn\_img \quad \text{[Mathematical Expression 6]}$$

(Step S307)

Figure 6:
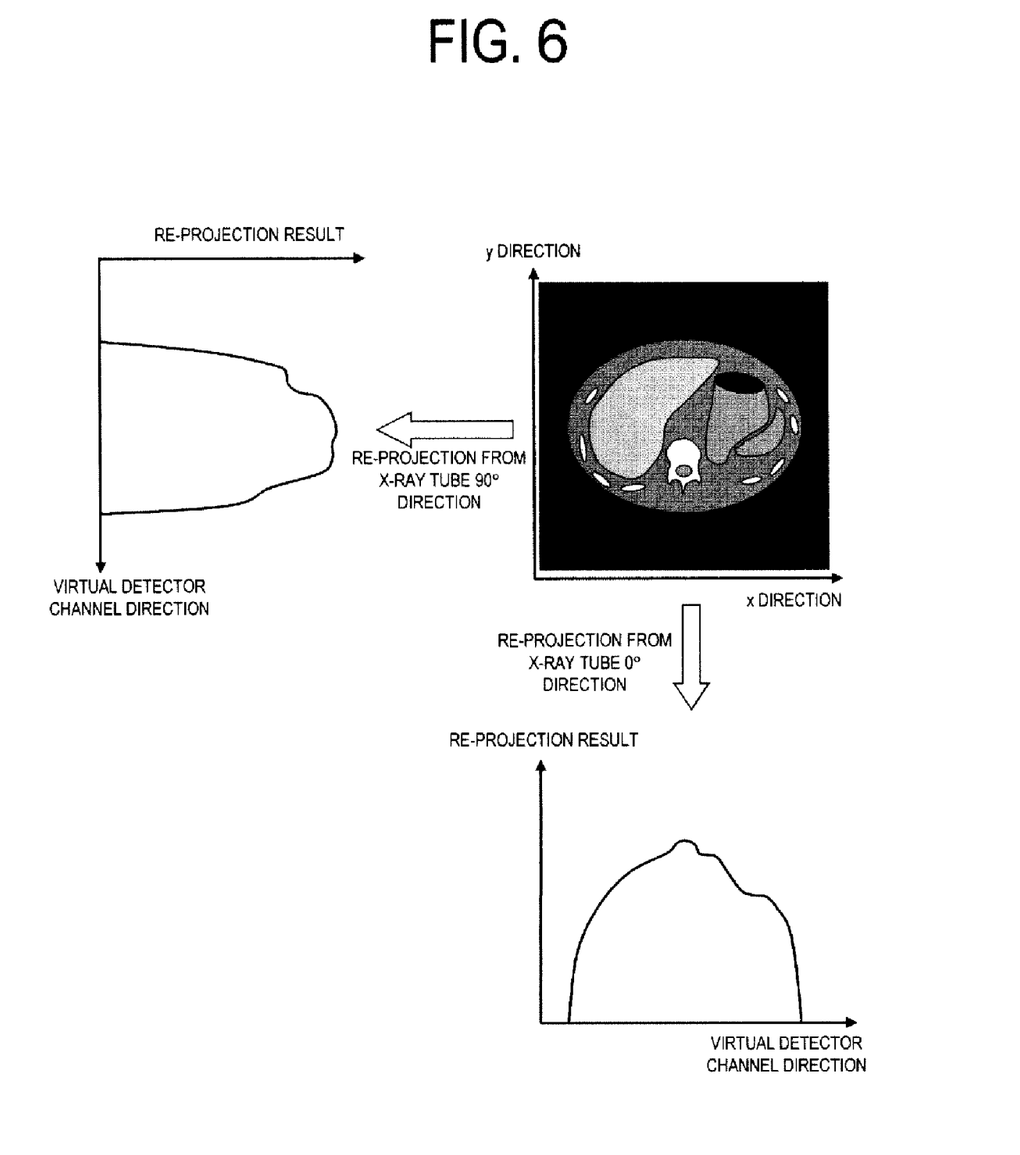
FIG. 6 is a diagram showing a reference projection data creating method.

The reference projection data creating means 204 creates reference projection data as shown in FIG. 6 by subjecting the reference image to re-projection processing. The same integration as the mathematical expression 1 or the mathematical expression 2 is executed in the re-projection processing. In FIG. 6, it is assumed that the state that the X-ray tube is located just above is set as 0° and the angle representing the position of the X-ray tube increases clockwise. For convenience of description, only re-projection results in two directions are shown. In the actual processing, it is desired to perform re-projection at the X-ray tube position in the same view as assumed scan or at the X-ray tube position in a view of a half round.

(Step S308)

The noise projection data creating means 205 creates the noise projection data on the basis of the virtual scan condition calculated in S306 and the reference projection data created in S307 as follows.

The product xmAs_ni between the tube current and the time for the noise image is represented by the mathematical expression 6. Furthermore, the value of the projection data is represented by prf, and the projection data noise Vr_ref(prf) when scanning is executed with some product xmAs_ref between some reference tube current and the time can be experimentally determined in advance. For example, the projection data noise can be represented by the mathematical expression 7.

$$Vr\_ref(prf) = c * \exp(a * prf) \quad \text{[Mathematical Expression 7]}$$

Here, c and a: constants which are experimentally determined in advance exp (x): exponential function for calculating x power of e of natural logarithm for argument x prf: value of projection data Accordingly, the variance value Vr_ni(vch) of the projection data of only the noise corresponding to the value of the reference projection data at some virtual channel vch can be calculated by the mathematical expression 8.

$$Vr\_ni(vch) = Vr\_ref(bsprf(vch)) * xmAs\_ref / xmAs\_ni \quad \text{[Mathematical Expression 8]}$$

Here, bsprf(vch): the value of reference projection data at virtual detector channel number vch That is, the projection data for which the average value at each channel of the virtual detector is equal to zero and the variance is represented by Vr_ni (vch) of the mathematical expression 8 is set as noise projection data.

By considering the value of the reference projection data created by re-projecting the reference image as described above, the noise projection data can be created in consideration of the effect of the distribution of the human body tissue in the reference image.

(Step S309)

The simulated lesion projection data creating means 206 can create the projection data of the simulated lesion on the basis of the preset condition of the simulated lesion (the coordinate, the size, the difference in CT value from the surrounding tissue) as follows.

It is assumed that the center coordinate of the simulated lesion, the diameter Dtum and the difference Htum in CT value between the stimulated lesion and the surrounding tissue is set through the condition setting screen, etc. for the simulated lesion shown in FIG. 4. The difference μc in X-ray attenuation coefficient between the simulated lesion and the surrounding tissue is determined from the difference Htum in CT value between the stimulated lesion and the surrounding tissue by the mathematical expression 9.

$$\mu c = \mu w * Htum/1000 \quad \text{[Mathematical Expression 9]}$$

Here,

μw: X-ray attenuation coefficient of water

Figure 7:
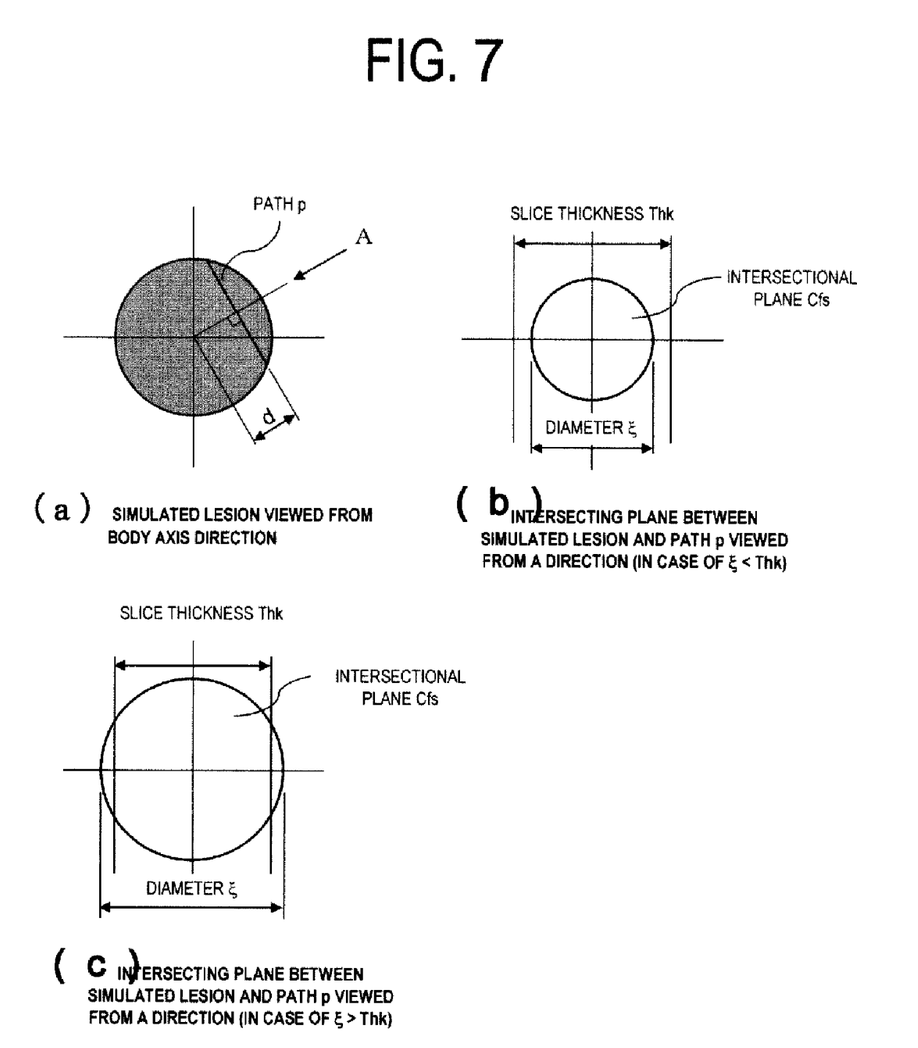
FIG. 7 is a diagram showing the relationship between a distribution of a simulated lesion in a slice thickness direction and an X-ray path.

Furthermore, in order to calculate the projection data in an X-ray path which is deviated from the center of the stimulated lesion by only a distance d, the distribution in the image slice thickness direction of the stimulated lesion is considered. That is, the X-ray path in a cross-sectional image which is viewed from the body axis direction is a line segment as shown in FIG. 7(a), however, it is necessary to consider that it actually has a plane having the depth corresponding to the slice thickness. The diameter ξ of the intersectional plane Cfs between the stimulated lesion and the X-ray path p shown in FIGS. 7(b) and (c) is represented by the mathematical expression 10.

$$\xi = 2 * \sqrt{\left(\frac{Dtum}{2}\right)^2 - d^2} \quad \text{[Mathematical Expression 10]}$$

In consideration of a case where the diameter ξ of the intersection plane between the simulated lesion and the X-ray path is smaller than the image slice thickness Thk as shown in FIG. 7(b), or a case of ξ=Thk (not shown) and a case where ξ>Thk as shown in FIG. 7(c), the value prftum(p) of the simulated lesion projection data in the X-ray path p is represented by the mathematical expression 11.

$$prftum(p) = \begin{cases} g * \frac{\mu c}{Thk} * \int_{z=-\xi/2}^{\xi/2} \sqrt{\left(\frac{\xi}{2}\right)^2 - z^2}\, dz & (\text{if } \xi \leq THK) \\ g * \frac{\mu c}{Thk} * \int_{z=-Thk/2}^{Thk/2} \sqrt{\left(\frac{\xi}{2}\right)^2 - z^2}\, dz & (\text{if } \xi > THK) \end{cases}$$

[Mathematical Expression 11]

Here, g: scale matching constant, this should be determined in advance.

(Step S310)

The projection data adding means 207 adds the noise projection data created in S308 with the simulated lesion projection data created in S309 to thereby create the projection data of an addition image.

(Step S311)

The image reconstructing means 208 applies a Filtered Back Projection method or the like to the projection data of the addition image created in S310 to reconstruct an image, thereby creating the addition image.

(Step S312)

The simulation image creating means 209 adds the addition image created in S311 to the reference image set in S302 or S303 to create a simulation image.

When the operator satisfies the simulation image created in S312 from the viewpoint of the visual effect of the image noise and the identification of the simulated lesion, the scan condition which implements the preset target image noise value may be used as a scan condition for the actual imaging operation. Here, the product xmAs_app between the tube current and the time to be applied as the scan condition for the actual imaging operation is represented by the mathematical expression 12.

$$xmAs\_app = xmAs0 * Vorg\_img/Vtgt \quad \text{[Mathematical Expression 12]}$$

The actual imaging operation is executed by applying the result of the mathematical expression 12, whereby an image suitable for diagnosis can be obtained. In order to apply the result of the mathematical expression 12 to the actual imaging operation, the result of the mathematical expression 12 which is displayed on the simulation image display device by the simulation image generating device 200 may be input through the input device 121 by the operator, or the simulation image generating device 200 may set the result of the mathematical expression 12 into the X-ray control device 110. When the simulation image generating device 200 sets the result of the mathematical expression 12 into the X-ray control device 110, the operation of the operator can be simplified.

A scan simulator program for making a computer implement the function described in the above embodiment may be constructed, and this program may be installed into a personal computer or a work station to implement the above function. In this case, the simulation image is not necessarily required to be displayed on the monitor of the personal computer or the work station in which the scan simulator program is installed, and a simulation image may be transmitted to a terminal device connected through a network such as LAN or the like to display the simulation image on the terminal device. With this construction, for example, based on the simulation image, a radiological technician as an operator of the X-ray CT apparatus asks an opinion about an imaging condition to a radiological doctor who is far away from the operating table of the X-ray CT apparatus. As a result, an image satisfying a radiological doctor's requirement who performs an image diagnosis can be picked up, and thus a more suitable image diagnosis can be performed.

FIG. 1
108 GANTRY CONTROL DEVICE
109 BED CONTROL DEVICE
110 X-RAY CONTROL DEVICE
122 IMAGE CALCULATING DEVICE
123 STORAGE DEVICE
124 SYSTEM CONTROL DEVICE
FIG. 2
201 OBJECT APPROXIMATE MODEL CALCULATING MEANS
202 IMAGE NOISE CALCULATING MEANS
203 ADDED NOISE AMOUNT CALCULATING MEANS
204 REFERENCE PROJECTION DATA CREATING MEANS
205 NOISE PROJECTION DATA CREATING MEANS
206 SIMULATED LESION PROJECTION DATA CREATING MEANS
207 PROJECTION DATA ADDING MEANS
208 IMAGE RECONSTRUCTING MEANS
209 SIMULATION IMAGE CREATING MEANS
210 IMAGE STORAGE DEVICE
220 CONDITION SETTING DEVICE (SETTING OF TARGET NOISE VALUE, SIMULATED LESION)
230 IMAGE DISPLAY DEVICE
FIG. 3
基準画像の設定 SETTING OF REFERENCE IMAGE
S301 IS PAST IMAGE PRESENT OR ABSENT?
有 PRESENT
無 ABSENT
S302 SET PAST IMAGE TO REFERENCE IMAGE

S303 SET HUMAN BODY PHANTOM IMAGE TO REFERENCE IMAGE

ノイズデータの生成 GENERATION OF NOISE DATA

S304 CALCULATE OBJECT APPROXIMATE MODEL

S305 CALCULATE IMAGE NOISE OF REFERENCE IMAGE

S306 CALCULATE ADDED NOISE AMOUNT AND VIRTUAL SCAN CONDITION

S307 CREATE REFERENCE PROJECTION DATA

S308 CREATE NOISE PROJECTION DATA

模擬病巣データの生成 GENERATION OF SIMULATED LESION DATA

S309 CREATE SIMULATED LESION PROJECTION DATA

シミュレーション画像の生成 GENERATION OF SIMULATION IMAGE

S310 CREATE PROJECTION DATA OF ADDITION IMAGE

S311 RECONSTRUCT IMAGE

S312 CREATE SIMULATION IMAGE

FIG. 4

基準画像 REFERENCE IMAGE y 方向 y DIRECTION x 方向 x DIRECTION

420 CONDITION FOR SIMULATED LESION 421 x COORDINATE 422 y COORDINATE

423 SIZE (DIAMETER)

424 DIFFERENCE OF CT VALUE

425 SHAPE: SPHERE

FIG. 5 y 方向 y DIRECTION x 方向 x DIRECTION

仮想的な検出器チャンネル方向 VIRTUAL DETECTOR CHANNEL DIRECTION x 方向積算値 x DIRECTION INTEGRATION VALUE y 方向積算値 y DIRECTION INTEGRATION VALUE

仮想的な検出器チャンネル方向 VIRTUAL DETECTOR CHANNEL DIRECTION y 方向の水近似透過長を算出 CALCULATE WATER APPROXIMATE TRANSMISSION LENGTH IN y DIRECTION

近似モデル決定 DETERMINE APPROXIMATE MODEL x 方向の水近似透過長を算出 CALCULATE WATER APPROXIMATE TRANSMISSION LENGTH IN x DIRECTION

FIG. 6

再投影結果 RE-PROJECTION RESULT

仮想的な検出器チャンネル方向 VIRTUAL DETECTOR CHANNEL DIRECTION

X 線管 90° 方向からの再投影 RE-PROJECTION FROM X-RAY TUBE 90° DIRECTION y 方向 y DIRECTION x 方向 x DIRECTION

X 線管 0° 方向からの再投影 RE-PROJECTION FROM X-RAY TUBE 0° DIRECTION

再投影結果 RE-PROJECTION RESULT

仮想的な検出器チャンネル方向 VIRTUAL DETECTOR CHANNEL DIRECTION

FIG. 7

(a) SIMULATED LESION VIEWED FROM BODY AXIS DIRECTION 経路 PATH p (b) INTERSECTING PLANE BETWEEN SIMULATED LESION AND PATH p VIEWED FROM A DIRECTION (IN CASE OF ξ<Thk)

スライス厚 SLICE THICKNESS Thk

交面 INTERSECTIONAL PLANE Cfs

直径 DIAMETER ξ

(c) INTERSECTING PLANE BETWEEN SIMULATED LESION AND PATH p VIEWED FROM A DIRECTION (IN CASE OF ξ>Thk)

スライス厚 SLICE THICKNESS Thk

交面 INTERSECTIONAL PLANE Cfs

直径 DIAMETER ξ

The invention claimed is:

1. An X-ray CT scan simulator, comprising:
a storing device for storing a reference image;
a setting device for setting a target noise value and a condition for a simulated lesion specified by an operator;
a simulated image generation device for generating a simulation image containing said simulated lesion; and
an image display device for displaying the simulation image containing the simulated lesion, wherein
said storing device further stores a first tube current and time for the reference image and a projection data noise as a function of a projection data where scanning is performed in a certain tube current and time, and wherein
said simulated image generation device further comprises:
a generating device for generating a noise image to be added based on a noise value for the reference image and the target noise value;
a calculating device for calculating second tube current and time for obtaining the noise image to be added based on the noise value for the reference image and the first tube current and time;
a reference projection data generating device for generating reference projection data by re-projecting the reference image;
a noise projection data generating device for generating noise projection data based on the function in the second tube current and time and the reference projection data;
a simulated lesion projection data generating device for generating a simulated lesion projection data in accordance with the condition for the simulated lesion, which (i) calculates a profile of the simulated lesion in a slice thickness direction, (ii) calculates an integral of the profile, and (iii) generates the simulation image by setting a value of the simulated lesion in accordance with the integral of the profile;
an projection data adding device for generating added projection data by adding the noise projection data and the simulated lesion projection data;
an image reconstructing device for reconstructing the added projection data and generating an image for addition including the simulated lesion; and a simulation image creating device for creating the simulation image by adding the reference image and the image for addition.

2. The X-ray CT scan simulator according to claim 1, wherein the condition for the lesion set by the setting device contains the position of the lesion, the size of the lesion and the contrast between the lesion and a surrounding tissue.

3. The X-ray CT scan simulator according to claim 2, wherein the setting device obtains a point indicated on the reference image as the position of the lesion.

4. An X-ray CT apparatus including:
an X-ray source for irradiating an object with X-ray,
an X-ray detector that is disposed so as to face the X-ray source and detects X-ray transmitted through the object,
a rotating device rotating around the object in which the X-ray source and the X-ray detector are mounted,
an image re-constructing device for re-constructing a tomogram of the object on the basis of transmitted X-ray doses in plural directions that are detected by the X-ray detector,
an imaging condition input device for inputting an irradiation condition of the X-ray and a condition for image reconstruction, and
an image display device for displaying the tomogram,
the X-ray CT apparatus further comprising:
a storing device for storing a reference image;
a setting device for setting a target noise value and a condition for a simulated lesion specified by an operator; and
a simulated image generation device for generating a simulation image containing said simulated lesion, wherein
said storing device further stores a first tube current and time for the reference image and a projection data noise as a function of a projection data where scanning is performed in a certain tube current and time, and wherein
said simulated image generation device further comprises:
  a generating device for generating a noise image to be added based on a noise value for the reference image and the target noise value;
  a calculating device for calculating second tube current and time for obtaining the noise image to be added based on the noise value for the reference image and the first tube current and time;
  a reference projection data generating device for generating reference projection data by re-projecting the reference image;
  a noise projection data generating device for generating noise projection data based on the function in the second tube current and time and the reference projection data;
  a simulated lesion projection data generating device for generating a simulated lesion projection data in accordance with the condition for the simulated lesion, which (i) calculates a profile of the simulated lesion in a slice thickness direction, (ii) calculates an integral of the profile, and (iii) generates the simulation image by setting a value of the simulated lesion in accordance with the integral of the profile;
  an projection data adding device for generating added projection data by adding the noise projection data and the simulated lesion projection data;
  an image reconstructing device for reconstructing the added projection data and generating an image for addition including the simulated lesion; and
  a simulation image creating device for creating the simulation image by adding the reference image and the image for addition, and wherein
the image display device displays the simulation image containing the simulated lesion.

5. The X-ray CT apparatus according to claim 4, further comprising an X-ray control device for controlling the X-ray source on the basis of an X-ray irradiation condition calculated when the simulated image generation device generates the simulation image.

6. The X-ray CT apparatus according to claim 4, wherein the condition for the lesion set by the setting device contains the position of the lesion, the size of the lesion and the contrast between the lesion and a surrounding tissue.

7. The X-ray CT apparatus according to claim 6, wherein the setting device obtains a point indicated on the reference image as the position of the lesion.

* * * * *